United States Patent [19]

Sands

[11] Patent Number: 4,664,158

[45] Date of Patent: May 12, 1987

[54] GROUNDING STRAP AND FABRIC AND METHOD

[75] Inventor: Timothy A. Sands, Hughesville, Pa.

[73] Assignee: C. M. Offray & Son, Inc., Chester, N.J.

[21] Appl. No.: 833,001

[22] Filed: Feb. 26, 1986

[51] Int. Cl.$^4$ .............................................. H05F 3/02
[52] U.S. Cl. ................................. 139/422; 139/425 R; 174/117 M; 174/129 R; 361/220
[58] Field of Search ................... 361/212, 220, 223; 57/901; 139/421, 422, 425 R; 174/117 M, 129 R

[56] References Cited

U.S. PATENT DOCUMENTS

| | | | |
|---|---|---|---|
| 4,557,968 | 12/1985 | Thornton et al. | 57/901 X |
| 4,577,256 | 3/1986 | Breidegam | 361/220 |

*Primary Examiner*—L. T. Hix
*Assistant Examiner*—Brian W. Brown

*Attorney, Agent, or Firm*—Mark T. Basseches; Paula T. Basseches

[57] ABSTRACT

An elastic conductive fabric for use as a grounding strap and the method of making the same are disclosed. The fabric is woven utilizing elastic yarn ends intermingled with conductive yarn ends. The weaving process is carried out while the elastic yarn ends are distended by at least 150% and preferably 250-400% as compared with the relaxed condition thereof. Preferably the conductive yarn is woven in a two over one pattern so that when tension is released in the elastic ends, the crests of the conductive ends which span two picks will project a substantial distance from the fabric surface. The opposite face of the fabric may be comprised of insulative ends likewise woven in a two over one pattern to provide enlarged crests at said face. Locking yarn ends maintain the conductive crests in a perpendicular condition relative to the fabric body.

4 Claims, 4 Drawing Figures

GROUNDING STRAP AND FABRIC AND METHOD

BACKGROUND OF THE INVENTION

1. Field of the Invention

The present invention is directed to a grounding strap and conductive stretchable fabric adapted to be formed into such strap.

More particularly, the invention relates to a stretchable conductive strap employed for the dissipation of electrostatic charges accumulating on the bodies of individuals.

2. The Prior Art

It is conventional practice for persons working in proximity to explosive environments or sensitive electronic devices to employ means for dissipating electrostatic charges. By way of example, operating room personnel working in proximity to explosive gas mixtures, computer operators, assemblers of electronic chips and the like generate static charges which, if not dissipated, could reach many thousands of volts. If such charges accumulate sufficiently, there is danger of a spark discharge to ground, with possible catastrophic consequences.

Numerous devices have been suggested to effect the desired dissipation, such devices including conductive wrist bands connected to ground.

U.S. Pat. No. 4,398,277 of Aug. 9, 1983, the content of which is herein incorporated by reference, embodies a comprehensive recitation of prior art devices employed for static dissipation and their shortcomings.

The noted patent discloses a knitted stretchable fabric wrist band which includes loops of an elastomeric yarn end plaited with a conductive end. The resultant wrist band is said to be advantageous in that, by virtue of the stretchability of the fabric, the surface of the fabric having conductive loops is drawn against the wrist of the wearer.

A drawback which inheres in the fabric of the noted patent resides in the fact that, notwithstanding the presence of loops of conductive yarn at one surface of the fabric, there is no assurance that the conductive components will provide an effective electrical connection to the skin of the wearer.

The difficulties inhering in the structure of the noted patent may be better appreciated when it is recognized that in large measure the static discharge straps are employed in controlled environments where temperature and humidity are carefully regulated. In such environments, and especially in environments wherein the humidity is maintained at a low level, effective grounding depends upon direct contact between the crests of the conductive loops and the skin of the wearer.

The problem is most acute in the case of male workers having substantial hair accumulation in the wrist area. In such cases the worker's hair may mat between the band and the skin, in effect providing an insulative sleeve which precludes proper static dissipation.

In the knitted fabric of said U.S. Pat. No. 4,398,277 the loops of conductive yarn tend to shrink in size when the fabric is stretched from the "as knit" condition and lie or be readily deflected to a condition in which they are disposed parallel to the skin of the wearer rather than normal thereto. The fabric structure of such patent lacks means for supporting the crests of the loops against deflection from the desired condition of perpendicularity. With continued use, the tendency of the loops of the fabric to lie in a parallel-to-the-skin, non-hair-penetrating condition increases as the fibers lose resilience. Moreover, as with all knitted fabrics, lengthwise stretching of the fabric results in a widthwise narrowing thereof.

Alternative proposed solutions to the grounding problem appear in U.S. Pat. Nos. 4,373,175 of Feb. 8, 1983; 4,459,633 of July 10, 1984, and 4,475,141 of Oct. 2, 1984. However all such prior art references are deficient in various aspects of comfort of the wearer and efficiency in effecting skin contact.

SUMMARY OF THE INVENTION

The present invention is directed to a fabric structure, method of manufacturing same, and body strap formed therefrom characterized in that the fabric includes a series of crests of conductive yarn ends which project a substantial distance from the matrix of the fabric and therefore will freely penetrate through the matted hair mass of the wearer into contact with the skin.

The invention is further directed to a method of making a fabric of the type described.

More particularly, in accordance with the invention there is formed a woven double-faced fabric, one face of which is comprised of non-conductive ends and the other face of which is comprised of conductive ends having crests projecting a significant distance from the fabric matrix. The insulative surface of the fabric assures that if the strap is accidentally contacted with a "live" source of electricity the source will not be connected to the wearer. The projecting crests of the conductive ends of the opposite side of the fabric assure good skin contact with the wearer, notwithstanding the wearer may have an accumulation of hair in the area of the strap.

Importantly, the structure of the fabric is such that the crests of the loops of conductive yarn ends are supported against deflection from the desired condition of perpendicularity to the main body of the fabric, thus assuring excellent skin contact through repeated use cycles.

In accordance with the invention the strap is woven utilizing a central series of elastomeric warp yarn ends. Conductive warp ends are woven in a two over one pattern to one side of the elastomeric ends, and insulative warp ends are woven in a two over one pattern to the other side of the elastomeric ends. Locking warp ends are woven to opposite sides of the elastomeric ends, the locking ends functioning to bind the insulative, conductive, and elastomeric ends to the filler picks, thus to prevent relative lengthwise shifting movement of the warp components.

A characterizing feature of the invention resides in weaving the fabric while maintaining the elastomeric ends in a highly distended and tensioned condition. Preferably the elastomeric ends are extended by a factor of at least about 150%. As a result of the tensioning of the elastomeric ends during weaving, when the tension is relieved the elastomeric ends will foreshorten to their relaxed concondition, with the result that the other warp yarns, and particularly the conductive and insulative warp yarns, will be caused to foreshorten in the axial direction of the fabric. As a result of such foreshortening, the elongate loops of conductive and insulative yarns will be displaced a significant distance from the opposite surfaces of the fabric. The thus projecting conductive crests are highly advantageous in that they are capable of penetrating through the matted hair of a wearer into contact with the wearer's skin. The effectiveness of penetration is enhanced by the fact that each time the elastic fabric is stretched to pass the band over the hand and onto the wrist of the wearer, the crests are retracted and then projected. Additionally, the locking yarns support the projecting crests against lateral deflection to assure maximum penetration.

The locking ends serve the further function of minimixing the likelihood that the crests of the conductive or insulative ends may become snagged in use.

It is accordingly an object of the invention to provide a novel method of weaving a fabric which is both stretchable and which includes a conductive surface.

It is a further object of the invention to provide a stretchable conductive fabric and a grounding strap made therefrom which provides effective electrical skin contact without necessitating a tight or constrictive encircling of the wrist of the wearer.

Still a further object of the invention is to provide a fabric and grounding strap made therefrom characterized in that the conductive crests project a significant distance from the fabric surface and are supported against lateral deflection by other components of the fabric structure, such other components also rendering the conductive ends resistant to snagging.

A still further object of the invention is to provide a method of manufacturing a fabric of the type described.

To attain these objects and such further objects as may appear herein or be hereinafter pointed out, reference is made to the accompanying drawings, forming a part hereof, in which.

Figure 1:
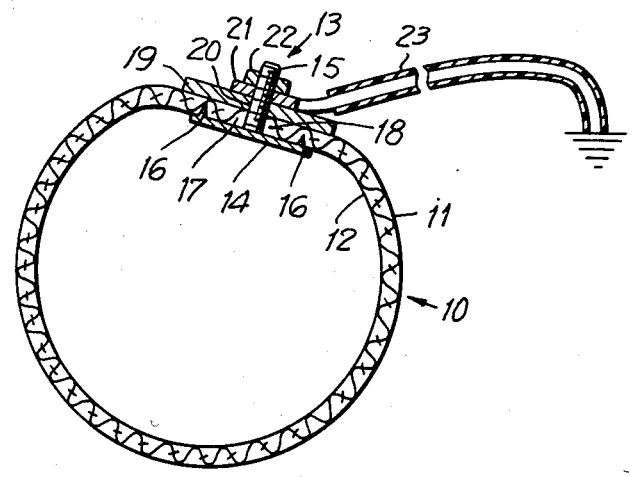
FIG. 1 is a sectional view of a grounding strap in accordance with the invention.

Referring now to the drawings, there is shown in FIG. 1 a grounding strap assembly 10 of representative construction, the strap including an outer surface 11 of cushioning but insulative nature, and an inner surface 12 comprised of conductive yarn ends. It will be appreciated that the illustrated fabric structure comprises the functional elements of the strap and need not extend across the entire width or length of the band. The strap may consist of a length of fabric formed into a band by a clip 13 which functions both as a mechanical fastener for the ends of the fabric strip and as an electrical connection to the inner conductive surface 12 of the strap.

The clip member forms no part of the instant invention and it will be readily recognized that numerous alternate constructions may be employed for effecting electrical contact to the surface 12 and for holding the fabric band in a circular configuration.

Additionally, separate mechanisms may be employed for the mechanical connecting and the electrical conducting functions. By way of illustration, clip 13 may include a conductive inner plate 14 having a threaded shank 15. A series of tangs 16 extend upwardly from the plate 14. A strip of fabric as hereinafter described is formed into a band or strap, the terminii 17, 18 of a conductive component of the strap being disposed adjacent the shank 15 and the tangs 16 extending into the body of the fabric. A stop plate 19 having an aperture 20 surrounding the shank 15 is disposed against the insulative surface 11 of the fabric. A grounding lug 21 is mounted over the shank and locked into position by a nut 22. The lug 21 is grounded as by insulated conductor 23. The connector assembly described may be covered by an insulative pad (not shown) where the strap may be used in proximity to exposed electrical mains.

Figure 4:
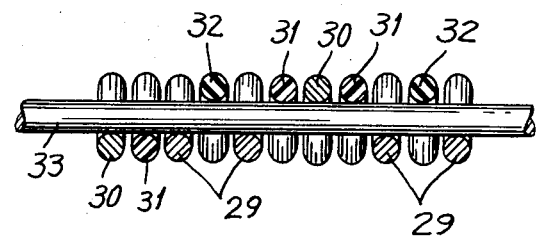
FIG. 4 is a fragmentary sectional view taken on line 4—4 of FIG. 1.
Figure 2:
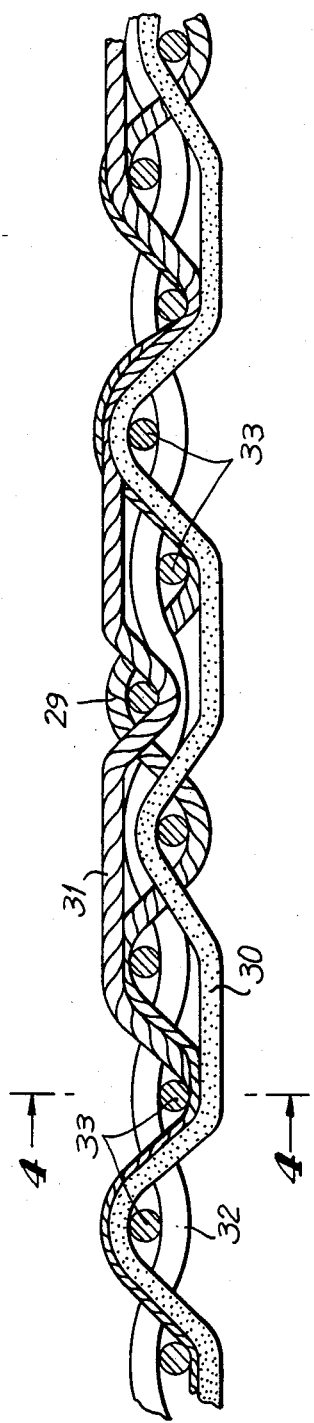
FIG. 2 is a schematic magnified cross section taken in the direction of the warp of the fabric showing the position of the yarn ends in the course of weaving.
Figure 3:
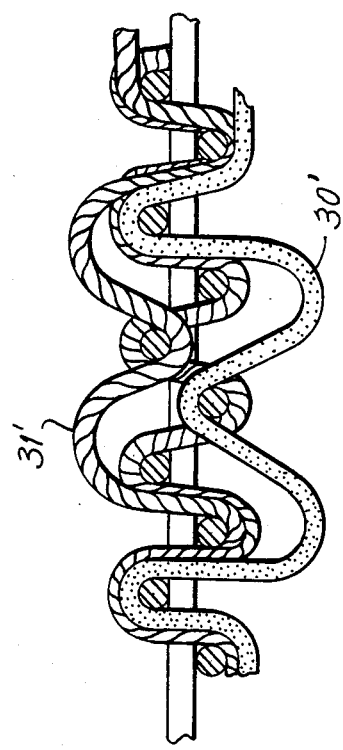
FIG. 3 is a view similar to FIG. 2 showing the fabric following weaving.

The advance of the present invention is directed to the fabric structure, a diagrammatic representative embodiment of which is illustrated in FIGS. 2, 3 and 4.

In accordance with the invention, the fabric is comprised of a series of warp yarn ends, namely locking yarn ends 29, conductive yarn ends 30, insulative ends 31 and elastomeric ends 32.

As will be understood by those skilled in the art the functional portion of the fabric as described herein may be flanked by other portions or extensions to provide decorative or like effects.

Referring now to FIGS. 2 through 4, in the fabric weave the elastomeric ends 32 run in a sinuous path over and under each of the alternate picks 33. The conductive ends 30 and insulative ends 31 are woven in a two over one pattern with the insulative ends spanning two picks at one surface of the fabric and the insulative ends 31 spanning two picks at the opposite surface of the fabric. Locking ends 29 are woven in a one over one pattern, with the crests of the locking ends being disposed to opposite sides of the picks from the elastic ends.

A characterizing feature of the fabric and the method of making the same resides in weaving the fabric while maintaining the elastomeric ends in a distended condition. The ends 32 are tensioned to a degree sufficient to distend the ends by a factor of from about 150% to 500% and preferably from 250 to 400%, resulting in a distension of the fabric of about 60 to 100% from the woven to the relaxed condition.

The locking ends function to hold the filling to the elastomeric ends in such manner as to assure that the insulative and conductive ends are keyed or connected to the elastomeric ends in such manner as to prevent axial shifting movement of the various warp ends relative to the picks at the interface of the noted components.

FIG. 4 represents a preferred sequence of the warp yarn ends. Alternative sequences may be employed.

When the tension of the elastomeric ends is released the elastomer will foreshorten in the direction of the warp to the configuration of FIG. 3 wherein the crests 30' of the conductive yarn ends will be deflected outwardly from the inner surface 12 of the fabric due to the two over one weave and foreshortening of the fabric.

In similar fashion the crests 31' of the insulative ends will be deflected outwardly from the outer surface 11 of the fabric. The degree of deflection of the crests 30' on the one hand the crests 31' on the other hand will in all instances be essentially constant due to the interaction previously referred to between the picks and the locking yarn ends.

The locking yarn ends serve the additional function of limiting or restricting the tendency of the conductive ends to deflect in a transverse direction, i.e. in a plane normal to that depicted in FIGS. 2 and 3. This rigidifying or stiffening effect is highly desirable in that, by retaining the conductive ends in a plane essentially perpendicular to the length of the strap, the crests 30' have an added tendency to penetrate through the hairs of the user to assure optimum skin contact.

The weave structure of the described fabric is additionally advantageous in that each time the fabric is distended, as is the case when a strap is passed over the hand of a wearer into the area of the wrist, the conductive crests will retract and be projected outwardly when the tension in the strap is released. The outward deflection of the conductive crests 30' at each application of the strap constitutes a further factor maximizing the likelihood that a major percentage of the conductive crests will penetrate through any hair mass of the wrist of the wearer and make good contact with the skin of the wearer.

The fabric structure may employ any of a variety of yarn ends. The conductive yarn ends are preferably comprised of a conventional yarn plated or coated with a conductive metallic material such as stainless steel or silver. As an alternative, conductive yarns comprised of polymeric materials having conductive filler such as carbon black may be employed. The metal plated or coated yarns are preferred due to their lower ohmic resistance. A preferred conductive yarn comprising a silver coated nylon is available from Sauquoit Industries Inc. of Scranton, Pa. under the trademark X-STATIC.

A further advantage of the fabric in accordance with the instant invention over conventional conductive fabrics of the types herein above described resides in the fact that the fabric in accordance with the invention preserves its low ohmic resistance characteristic over a multiplicity of cycles of stretching and relaxation.

By way of example, tests were conducted by using a test procedure of clamping a 2½" length of fabric in accordance with the invention between two clamps and stretching the fabric to elongate the same by a factor of 100%, i.e. to 5". The testing procedure involved elongation at the rate of 155 stretching cycles per minute until the fabric was subjected through a total of 350,000 cycles of elongation and relaxation. The ohmic resistance of a 1½" increment of the treated fabric was periodically measured.

The results of the tests are shown in the chart below. 1 and 2 constitute fabrics as described hereinabove. 3 and 4 constitute commercially available fabrics utilized in wrist strap grounding applications.

In all instances the numbers beneath the fabric identification represent the measured resistance in ohms.

| Cycles | Fabric 1 | Fabric 2 | Fabric 3 | Fabric 4 |
| --- | --- | --- | --- | --- |
| 0 | 40 | 155 | 120 | 155 |
| 9000 | 140 | 85 | 57 | 320 |
| 18000 | 135 | 42 | 108,000 | 583 |
| 27000 | 130 | 79 | 120,000 | 1100 |
| 350000 | 103 | 64 | 802,000 | 2520 |

The above experiment is considered clearly to demonstrate the ability of the fabric in accordance with the invention to withstand multiple cycles of extension and contraction as might be expected to be experienced when the strap is stretched for application and relaxed in use, without loss of effectiveness, the fabric of the invention indeed evincing unexpected and unexplained reduction in resistance with repeated cycling. In contrast, the competitive fabrics tested evinced significant increases in resistance following repeated cycling.

It will be apparent to those skilled in the art that numerous variations in details of construction may be made without departing from the spirit of the invention. As above noted, the pattern or sequence of warp threads may be varied, as may the number of warp sequences, yarn compositions and the like. Accordingly the invention is to be broadly construed within the scope of the appended claims.

Having thus described the invention and illustrated its use, what is claimed as new and is desired to be secured by Letters Patent is:

1. The method of manufacturing a woven fabric strip for use as a grounding strap or the like comprising the steps of providing a plurality of elastomeric warp ends, conductive warp ends, insulative warp ends, and locking yarn ends, providing a filler yarn, weaving said filler yarn through said warp ends to define a fabric structure in which said conductive yarn spans two picks of said filler yarn at one surface of said strip and one said pick at the other surface of said strip, said insulative yarn spans two said picks at said other surface and one said pick at said one surface of said strip, a said locking end and an elastomeric end each passes above and below alternate said picks, adjacent said locking and elastomeric yarns lying to opposite sides of said picks, said weaving step being effected while said elastomeric yarn ends are maintained in a distended condition whereat said yarn ends are elongated in the range of from about 150% to 500% as compared with the relaxed condition thereof while said remaining warp ends remain substantially undistended during said weaving step, whereby upon release of tension in said elastomeric ends, said fabric is foreshortened in the range of from about 60% to 100% as compared to the as-woven condition, thereby to deflect crests of said conductive ends from said one surface and said insulating ends from said other surface.

2. The method in accordance with claim 1 wherein said filler yarn is applied under a tension sufficient to lock said warp ends against relative sliding movement in the direction of the warp at the interface of said warp ends and said picks.

3. A woven conductive fabric for forming an elastic grounding strip comprising a plurality of elastomeric warp ends, a plurality of conductive warp ends, a plurality of insulative warp ends, and a plurality of locking warp ends, filler yarn picks disposed transversely of said warp ends, said conductive warp ends being arrayed in a pattern wherein said ends span two picks of said filler yarn at one surface of said fabric and one pick at the other surface of said fabric, said insulative warp ends being arrayed in a pattern wherein said ends span two said picks at said other surface of said fabric and one said pick at said one surface, said locking ends and said elastomeric ends passing in a sinuous pattern above and below each alternate said pick, adjacent said locking and elastomeric ends lying to opposite sides of said picks, said elastomeric ends during weaving being maintained in a distended condition when woven of about 150% to 500% as compared with the relaxed condition thereof while said other warp ends during weaving being substantially undistended whereby, upon relaxation and foreshortening of said elastomeric ends said fabric as a whole is foreshortened by a factor of from about 60% to 100% as compared to the as-woven condition, thereby to deflect crests of said conductive and insulative ends outwardly from said one and said other surfaces respectively.

4. A woven fabric in accordance with claim 3 wherein said picks are tensioned to lock said yarn ends against relative sliding movement in the direction of the warp of said fabric at the interface of said picks and said warp ends.

* * * * *